US010422915B2

(12) United States Patent
Jachmann et al.

(10) Patent No.: US 10,422,915 B2
(45) Date of Patent: Sep. 24, 2019

(54) EXTERNAL HOUSING FOR SIGNAL TO NOISE IMPROVEMENT

(71) Applicant: Halliburton Energy Services, Inc., Houston, TX (US)

(72) Inventors: Rebecca Corina Jachmann, Spring, TX (US); Jie Yang, Paoli, PA (US); Daniel Lee Miller, Kingwood, TX (US)

(73) Assignee: Halliburton Energy Services ,Inc., Houston, TX (US)

( * ) Notice: Subject to any disclaimer, the term of this patent is extended or adjusted under 35 U.S.C. 154(b) by 77 days.

(21) Appl. No.: 15/524,955

(22) PCT Filed: Dec. 29, 2015

(86) PCT No.: PCT/US2015/067852
§ 371 (c)(1),
(2) Date: May 5, 2017

(87) PCT Pub. No.: WO2017/116415
PCT Pub. Date: Jul. 6, 2017

(65) Prior Publication Data

US 2018/0292562 A1 Oct. 11, 2018

(51) Int. Cl.

| | |
|---|---|
| ***G01V 3/32*** | (2006.01) |
| ***G01V 3/14*** | (2006.01) |
| ***G01N 24/08*** | (2006.01) |
| ***G01R 33/341*** | (2006.01) |
| ***G01R 33/38*** | (2006.01) |
| ***G01R 33/3873*** | (2006.01) |

(52) U.S. Cl.
CPC ............ *G01V 3/32* (2013.01); *G01N 24/081* (2013.01); *G01R 33/341* (2013.01); *G01R 33/3808* (2013.01); *G01R 33/3873* (2013.01); *G01V 3/14* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,432,667 | A | 3/1969 | Caldwell | |
| 5,095,271 | A * | 3/1992 | Ohkawa ............ | G01R 33/3808 324/300 |
| 6,326,785 | B1 | 12/2001 | Kruspe | |
| 6,445,180 | B1 | 9/2002 | Reiderman et al. | |
| 7,834,622 | B2 | 11/2010 | Reiderman et al. | |
| 7,859,260 | B2 | 12/2010 | Reiderman | |

(Continued)

FOREIGN PATENT DOCUMENTS

| | | | |
|---|---|---|---|
| WO | WO 2009/088548 | A2 | 7/2009 |
| WO | WO 2012/068219 | A2 | 5/2012 |

OTHER PUBLICATIONS

International Search Report and the Written Opinion of the International Search Authority, or the Declaration, dated Aug. 24, 2016, PCT/US2015/067852, 16 pages, ISA/KR.

*Primary Examiner* — Tung X Nguyen
*Assistant Examiner* — Dominic E Hawkins

(57) ABSTRACT

Nuclear magnetic resonance apparatuses and systems are described. In an example, the apparatus comprises a tool housing and a magnet assembly disposed within the tool housing to produce a magnetic field in a volume in a geological formation. An external housing containing an antenna assembly is coupled to the tool housing.

20 Claims, 7 Drawing Sheets

WELL SYSTEM 100a
COMPUTING SYSTEM 110
LOGGING SYSTEM 108
SURFACE EQUIPMENT 112
WELL HEAD 105
SURFACE 106
WELLBORE 104
LOGGING TOOL 102
120 SUBTERRANEAN REGION
122

WELL SYSTEM 100b
132
112
110
134
105
106
120
104
102

(56) References Cited

U.S. PATENT DOCUMENTS

| | | | | |
|---|---|---|---|---|
| 9,181,798 | B2* | 11/2015 | Palaghita | E21B 17/028 |
| 2003/0085707 | A1* | 5/2003 | Minerbo | G01V 3/28<br>324/343 |
| 2004/0183533 | A1 | 9/2004 | Edwards et al. | |
| 2005/0257610 | A1* | 11/2005 | Gillen | E21B 47/00<br>73/152.02 |
| 2006/0255799 | A1* | 11/2006 | Reiderman | G01N 24/081<br>324/303 |
| 2010/0188080 | A1* | 7/2010 | Kruspe | G01V 3/32<br>324/303 |
| 2013/0009645 | A1* | 1/2013 | Miki | G01R 33/307<br>324/322 |
| 2014/0285190 | A1* | 9/2014 | Allen | G01V 3/32<br>324/303 |
| 2015/0061664 | A1* | 3/2015 | Reiderman | G01V 3/32<br>324/303 |
| 2015/0061665 | A1* | 3/2015 | Reiderman | G01V 3/32<br>324/303 |

* cited by examiner

EXTERNAL HOUSING FOR SIGNAL TO NOISE IMPROVEMENT

BACKGROUND

In the field of logging (e.g., wireline logging, logging while drilling (LWD) and measurement while drilling (MWD)), nuclear magnetic resonance (NMR) tools have been used to explore geographic formations based on the magnetic interactions with subsurface material. Some downhole NMR tools include a magnet assembly that produces a static magnetic field, and a coil assembly that generates radio frequency (RF) controls signals and detects magnetic resonance phenomena in the subsurface material. Properties of the subsurface can be identified from the detected phenomena.

DETAILED DESCRIPTION

The following detailed description refers to the accompanying drawings that show, by way of illustration and not limitation, various embodiments in which the invention may be practiced. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

In nonhomogeneous magnetic fields, the NMR signal comes from a limited region of the sample being measured, which is termed the "sensitive volume." NMR signals are intrinsically weak signals based on the natural polarization of spins in the sensitive volume to be measured. When using NMR-based logging tools, it can be difficult to achieve a satisfactory signal to noise ratio (SNR) based on the natural polarization of the magnetic nuclear spins. In addition, the ex situ (i.e., outward looking) nature of downhole NMR logging tools means that the excitation field naturally falls off in strength over distance from the tool. Thus, the further a receiving antenna is from the sensitive volume, the lower the amplitude of the corresponding received signal. Further, the presence of conductive fluids surrounding downhole NMR-based logging tools in the borehole can diminish the quality of received signals. The conductivity of these fluids can cause losses due to, for example, Johnson noise.

In some embodiments, a NMR-based tool can be constructed to provide subsurface data with an improved signal to noise ratio. For example, a tool constructed according to various embodiments disclosed herein may include an external housing coupled to the tool housing to serve as a fluid excluder and to provide a higher signal to noise ratio than conventional tools can offer. Some examples include an apparatus comprising a tool housing and a magnet assembly disposed within the tool housing to produce a magnetic field in a volume in a geological formation. An external housing containing an antenna assembly is coupled to the tool housing. These and other embodiments will now be described in detail.

Figure 1A:
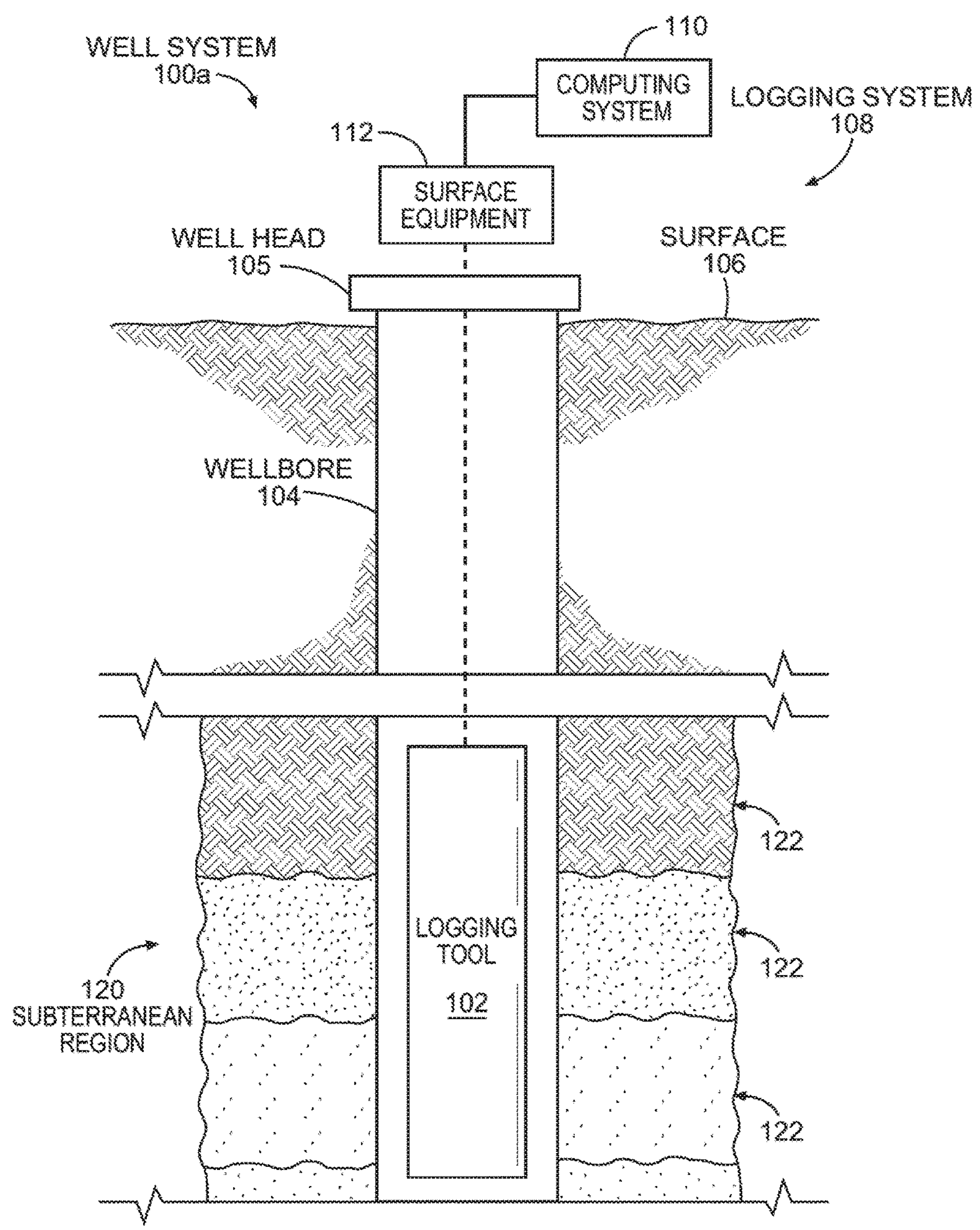
FIG. 1A is a diagram of an example well system, according to various embodiments.

FIG. 1A is a diagram of an example well system 100*a*. The example well system 100*a* includes an NMR logging system 108 and a subterranean region 120 beneath the ground surface 106. A well system can include additional or different features that are not shown in FIG. 1A. For example, the well system 100*a* may include additional drilling system components, wireline logging system components, etc.

The subterranean region 120 can include all or part of one or more subterranean formations or zones. The example subterranean region 120 shown in FIG. 1A includes subsurface layers 122 and a wellbore 104 penetrated through the subsurface layers 122. The subsurface layers 122 can include sedimentary layers, rock layers, sand layers, or combinations of these and other types of subsurface layers. One or more of the subsurface layers can contain fluids, such as brine, oil, gas, etc. Although the example wellbore 104 shown in FIG. 1A is a vertical wellbore, the NMR logging system 108 can be implemented in other wellbore orientations. For example, the NMR logging system 108 may be adapted for horizontal wellbores, slanted wellbores, curved wellbores, vertical wellbores, or combinations of these.

The example NMR logging system 108 includes a logging tool 102, surface equipment 112, and a computing subsystem 110. In the example shown in FIG. 1A, the logging tool 102 is a downhole logging tool that operates while disposed in the wellbore 104. The example surface equipment 112 shown in FIG. 1A operates at or above the surface 106, for example, near the well head 105, to control the logging tool 102 and possibly other downhole equipment or other components of the well system 100. The example computing subsystem 110 can receive and analyze logging data from the logging tool 102. An NMR logging system can include additional or different features, and the features of an NMR logging system can be arranged and operated as represented in FIG. 1A or in another manner.

In some instances, all or part of the computing subsystem 110 can be implemented as a component of, or can be integrated with one or more components of, the surface equipment 112, the logging tool 102 or both. In some cases, the computing subsystem 110 can be implemented as one or more computing structures separate from the surface equipment 112 and the logging tool 102.

In some implementations, the computing subsystem 110 is embedded in the logging tool 102, and the computing subsystem 110 and the logging tool 102 can operate concurrently while disposed in the wellbore 104. For example, although the computing subsystem 110 is shown above the surface 106 in the example shown in FIG. 1A, all or part of the computing subsystem 110 may reside below the surface 106, for example, at or near the location of the logging tool 102.

The well system 100*a* can include communication or telemetry equipment that allows communication among the computing subsystem 110, the logging tool 102, and other components of the NMR logging system 108. For example, the components of the NMR logging system 108 can each include one or more transceivers or similar apparatus for wired or wireless data communication among the various components. For example, the NMR logging system 108 can include systems and apparatus for optical telemetry, wireline telemetry, wired pipe telemetry, mud pulse telemetry, acoustic telemetry, electromagnetic telemetry, or a combination of these and other types of telemetry. In some cases, the logging tool 102 receives commands, status signals, or other types of information from the computing subsystem 110 or another source. In some cases, the computing subsystem 110 receives logging data, status signals, or other types of information from the logging tool 102 or another source.

NMR logging operations can be performed in connection with various types of downhole operations at various stages in the lifetime of a well system. Structural attributes and components of the surface equipment 112 and logging tool 102 can be adapted for various types of NMR logging operations. For example, NMR logging may be performed during drilling operations, during wireline logging operations, or in other contexts. As such, the surface equipment 112 and the logging tool 102 may include, or may operate in connection with drilling equipment, wireline logging equipment, or other equipment for other types of operations.

In some implementations, the logging tool 102 includes a magnet assembly that includes a central magnet and two end piece magnets. The end piece magnets can be spaced apart from the axial ends of the central magnet. The end pieces together with the central magnet can define four magnetic poles, which may be arranged to enhance the static magnetic field in a volume of interest. In some cases, the central magnet defines a first magnetic field orientation, and the end piece magnets define a second magnetic field orientation that is orthogonal to the first magnetic field orientation. In some implementations, the logging tool 102 includes a magnet assembly that produces a magnetic field in multiple distinct sub-volumes in the subterranean region 120.

The logging tool 102 can also include multiple, orthogonal transversal-dipole antennas. The orthogonal transversal-dipole antennas can produce circular polarized excitation in a subterranean volume and acquire a response from the volume by quadrature coil detection. The logging tool 102 can also include multiple antenna assemblies at respective locations along the longitudinal axis. Each of the antenna assemblies can detect an NMR response from a respective one of the distinct sub-volumes. Alternatively, the logging tool can include multiple longitudinal-dipole antennas.

In some implementations, the logging tool 102 includes a magnet assembly and a transversal-dipole and monopole antenna assembly. The transversal-dipole and monopole antenna assembly can obtain a unidirectional azimuthally-selective NMR response from a subterranean volume about the magnet assembly. The transversal-dipole and monopole antenna assembly can include orthogonal transversal-dipole antennas and a monopole antenna.

Figure 1B:
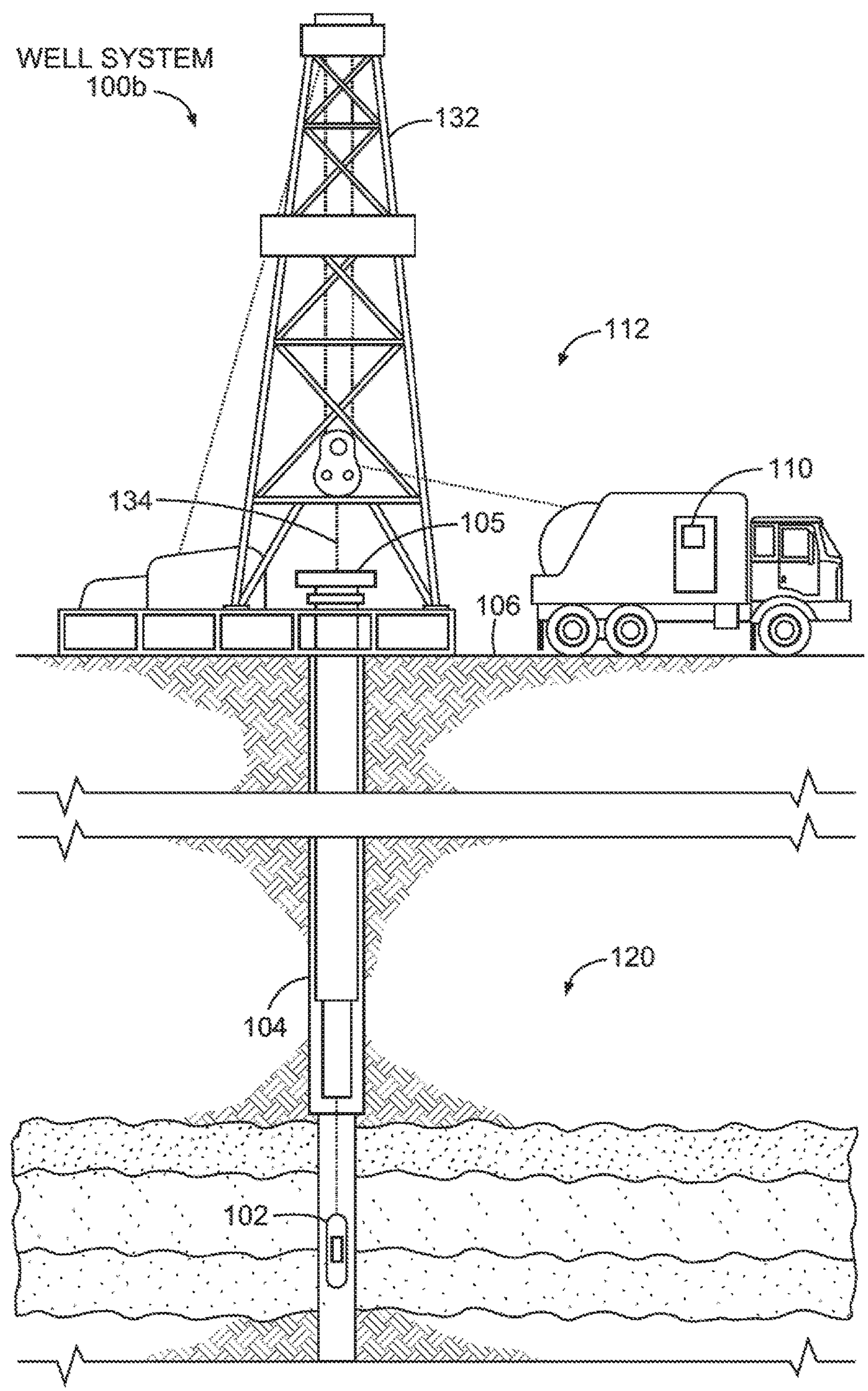
FIG. 1B is a diagram of an example well system that includes an NMR tool in a wireline logging environment, according to various embodiments.

In some examples, NMR logging operations are performed during wireline logging operations. FIG. 1B shows an example well system 100*b* that includes the logging tool 102 in a wireline logging environment. In some example wireline logging operations, the surface equipment 112 includes a platform above the surface 106 equipped with a derrick 132 that supports a wireline cable 134 that extends into the wellbore 104. Wireline logging operations can be performed, for example, after a drill string is removed from the wellbore 104, to allow the wireline logging tool 102 to be lowered by wireline or logging cable into the wellbore 104.

Figure 1C:
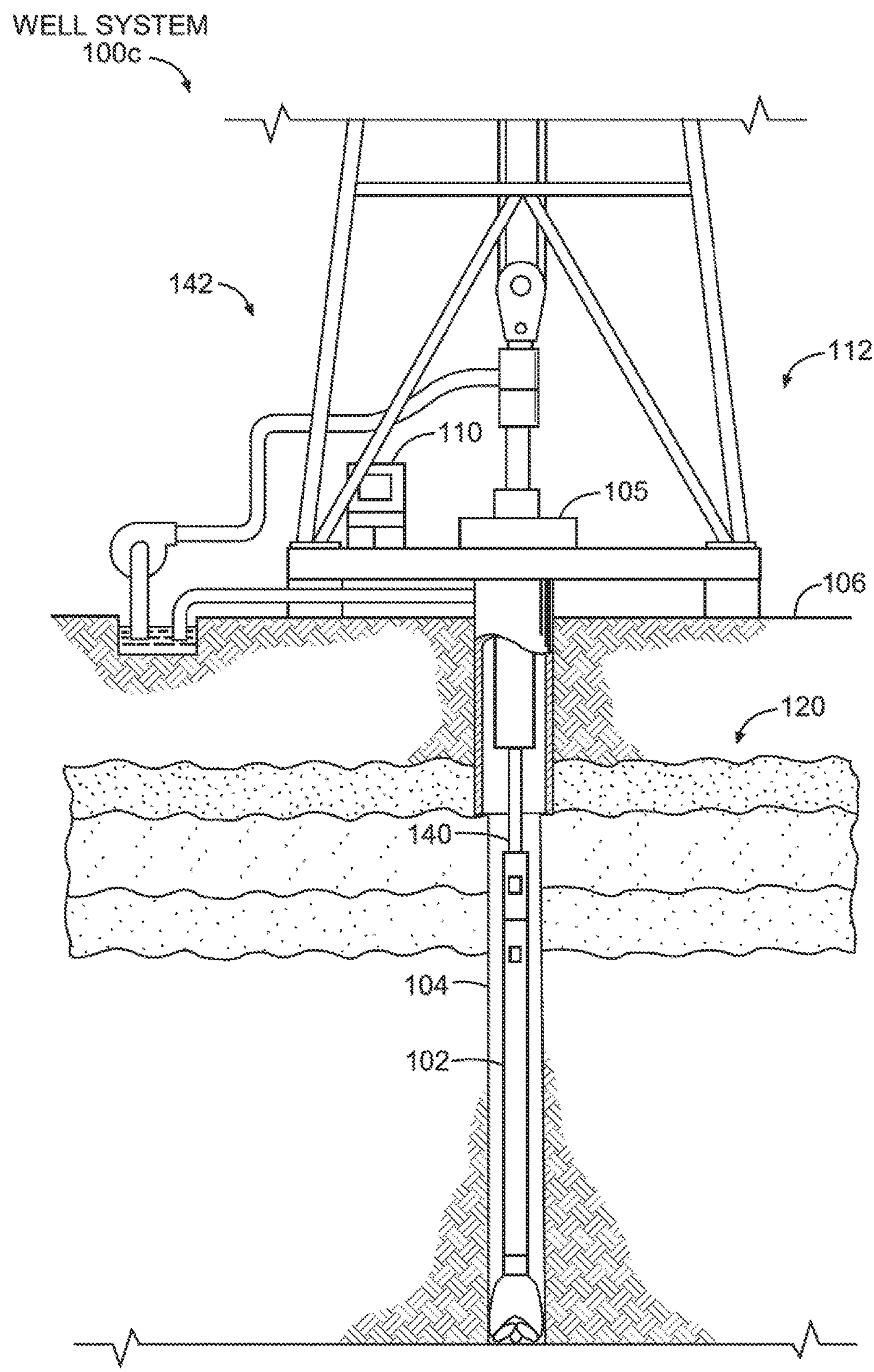
FIG. 1C is a diagram of an example well system that includes an NMR tool in a logging while drilling (LWD) environment, according to various embodiments.

In some examples, NMR logging operations are performed during drilling operations. FIG. 1C shows an example well system 100*c* that includes the logging tool 102 in a logging while drilling (LWD) environment. Drilling is commonly carried out using a string of drill pipes connected together to form a drill string 140 that is lowered through a rotary table into the wellbore 104. In some cases, a drilling rig 142 at the surface 106 supports the drill string 140, as the drill string 140 is operated to drill a wellbore penetrating the subterranean region 120. The drill string 140 may include, for example, a kelly, drill pipe, a bottomhole assembly, and other components. The bottomhole assembly on the drill string may include drill collars, drill bits, the logging tool 102, and other components. The logging tools may include measuring while drilling (MWD) tools, LWD tools, and others.

In some implementations, the logging tool 102 includes an NMR tool for obtaining NMR measurements from the subterranean region 120. As shown, for example, in FIG. 1B, the logging tool 102 can be suspended in the wellbore 104 by a coiled tubing, wireline cable, or another structure that connects the tool to a surface control unit or other components of the surface equipment 112. In some example implementations, the logging tool 102 is lowered to the bottom of a region of interest and subsequently pulled upward (e.g., at a substantially constant speed) through the region of interest. As shown, for example, in FIG. 1C, the logging tool 102 can be deployed in the wellbore 104 on jointed drill pipe, hard wired drill pipe, or other deployment hardware. In some example implementations, the logging tool 102 collects data during drilling operations as it moves downward through the region of interest. In some example implementations, the logging tool 102 collects data while the drill string 140 is moving, for example, while it is being tripped in or tripped out of the wellbore 104.

In some implementations, the logging tool 102 collects data at discrete logging points in the wellbore 104. For example, the logging tool 102 can move upward or downward incrementally to each logging point at a series of depths in the wellbore 104. At each logging point, instruments in the logging tool 102 perform measurements on the subterranean region 120. The measurement data can be communicated to the computing subsystem 110 for storage, processing, and analysis. Such data may be gathered and analyzed during drilling operations (e.g., during logging while drilling (LWD) operations), during wireline logging operations, or during other types of activities.

The computing subsystem 110 can receive and analyze the measurement data from the logging tool 102 to detect properties of various subsurface layers 122. For example, the computing subsystem 110 can identify the density, viscosity, porosity, material content, or other properties of the subsurface layers 122 based on the NMR measurements acquired by the logging tool 102 in the wellbore 104.

In some implementations, the logging tool 102 obtains NMR signals by polarizing nuclear spins in the subterranean region 120 and pulsing the nuclei with a radio frequency (RF) magnetic field. Various pulse sequences (i.e., series of radio frequency pulses, delays, and other operations) can be used to obtain NMR signals, including the Carr Purcell Meiboom Gill (CPMG) sequence (in which the spins are first tipped using a tipping pulse followed by a series of refocusing pulses), the Optimized Refocusing Pulse Sequence (ORPS) in which the refocusing pulses are less than 180°, a saturation recovery pulse sequence, and other pulse sequences.

The acquired spin-echo signals (or other NMR data) may be processed (e.g., inverted, transformed, etc.) to a relaxation-time distribution (e.g., a distribution of transverse relaxation times $T_2$ or a distribution of longitudinal relaxation times $T_1$), or both. The relaxation-time distribution can be used to determine various physical properties of the formation by solving one or more inverse problems. In some cases, relaxation-time distributions are acquired for multiple logging points and used to train a model of the subterranean region. In some cases, relaxation-time distributions are acquired for multiple logging points and used to predict properties of the subterranean region.

Figure 2:
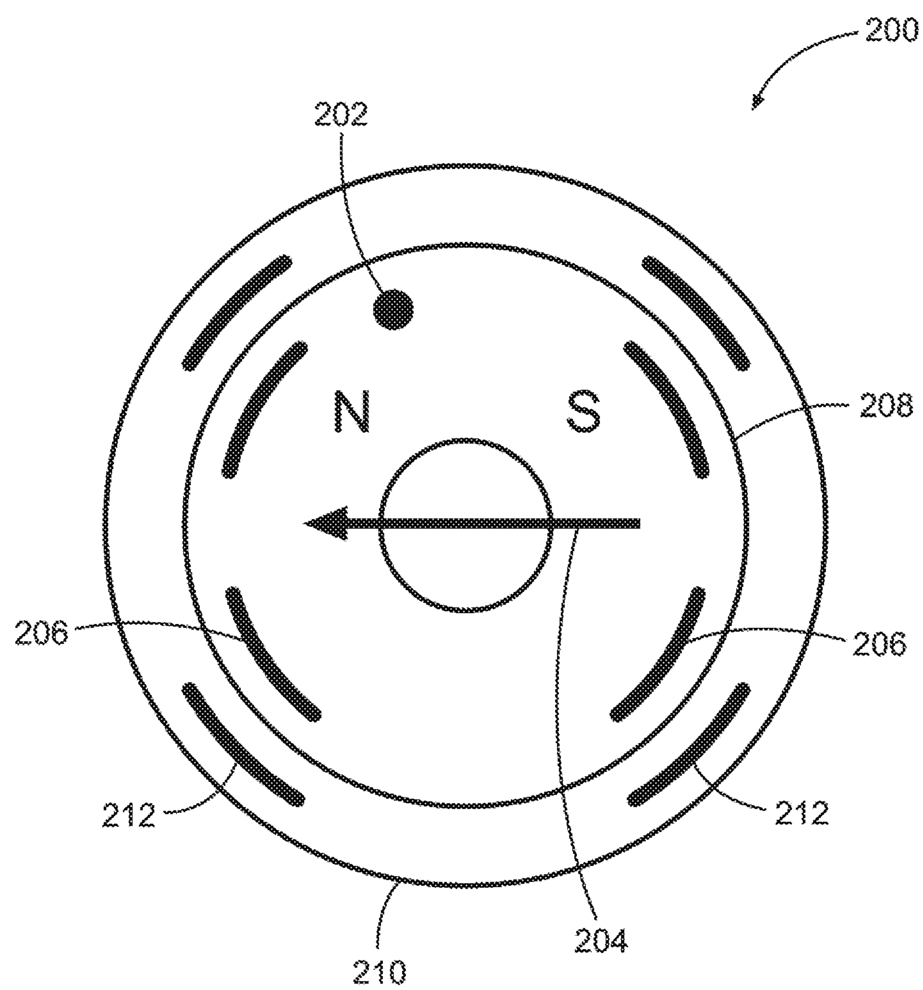
FIG. 2 is a cross-sectional view of an example NMR tool, according to various embodiments.

FIG. 2 is a cross-sectional view of an example NMR tool 200, according to one or more embodiments. In use, the NMR tool 200 can be lowered into a borehole to examine properties of the geological formation in the vicinity of the borehole. The NMR tool 200 includes a magnet assembly 202 that generates a static magnetic field to produce polarization in a volume of investigation (e.g., a geological formation surrounding the borehole). FIG. 2 illustrates an example magnetization direction 204 of the magnet assembly 202.

The NMR tool 200 also includes an antenna assembly 206 that generates a radio frequency (RF) magnetic field to generate excitation, and also acquires NMR signals. The antenna assembly 206 can comprise a transversal-dipole antenna or a longitudinal-dipole antenna. In this example, the magnet assembly 202 and the antenna assembly 206 are disposed within a tool housing 208. An external housing 210 is removably coupled to the tool housing 208. As illustrated, the external housing 210 is positioned circumferentially disposed around an exterior surface of the tool housing 208. The external housing 210 can comprise a number of antennas, magnets, and/or permeable material, but has at least one of the three. In other words, at least one component of the NMR tool 200 is housed within the external housing 210 portion of the tool. In this example, the external housing 210 includes an external antenna assembly 212. Although the external housing 210 shown in FIG. 2 has a circular outer diameter, the external housing 210 can be implemented with any outward shape capable of fitting into a borehole. The external housing 210 acts as an external sleeve that encases the tool housing 208 section of the NMR tool 200.

The magnet assembly 202 can comprise multiple unitary ring-shaped elements, a series of rectangular elements placed into a ring-shaped arrangement, or some arbitrary shape (e.g., triangular, square, or ellipse). It is noted that materials often change shape when in the presence of a magnetic field and then return to its original shape when the magnetic field is removed. In pulsing magnetic fields (e.g., from the antenna assembly), each RF power pulse deforms the magnet, which then returns to its original shape when the pulse ends. This property is referred to as magnetostriction. Mechanical oscillations induced by magnetostriction, termed magnetostrictive ringing (hereinafter, "ringing"), result in undesired noise.

Rectangular-shaped slates of ferrite material (e.g., a soft magnetic composite material) can be placed and glued together into a ring-shaped arrangement, which reduces the effects of ringing. Some magnetic materials, such as samarium-cobalt magnets, are conductive and would ring without both a copper shield and a magnetically permeable material placed in-between the magnet and antenna assembly to minimize penetration of the magnetic field. Copper can be used to shield magnets from RF antenna pulses and reduce antenna field penetration into the magnet, which might otherwise cause ringing. Ferrite materials are generally both ferromagnetic and electrically nonconductive. The pieced together ferrite magnet does not ring in pulsing magnetic fields, and thus, does not require the use of permeable materials as part of the magnet assembly.

In the example of FIG. 2, the magnet assembly rings at a predetermined, acceptable level and does not have any components shielding the magnet assembly from a pulsing RF field generated by either the antenna assembly or the external antenna assembly. The external antenna assembly is communicably coupled to a lead (not shown) from within the tool housing 208, allowing the external antenna assembly to be electrically attached to electronics (e.g., transmitters, receivers, amplifiers, or pre-amplifiers) within the tool housing 208. It is noted that in some embodiments, the antenna assembly within tool housing 208 can be deactivated when the external antenna assembly becomes communicably coupled to the tool housing 208. The external housing 210 should be sufficiently coupled to the tool housing 208 to prevent borehole fluids from entering. This can be accomplished with an O-ring positioned between the external housing 210 and the tool housing 208 to create a seal at their interface, or any other method of making fluid tight seals.

When antennas are located in the external housing 210, the antenna assembly becomes located closer to the sensitive volume. For example, external antenna assembly 212 is closer to the outside of NMR tool 200 than antenna assembly 206 due to the increased outer diameter. As a result, any received signals will increase in strength. The NMR tool 200 can be operated with a shallower depth of investigation (DOI) by using the external antenna assembly than tools without an external housing. The DOI is defined as the distance from the borehole wall to the NMR sensitive region (also known as the sensitive volume), and can be changed by the addition of magnets or permeable material to the NMR tool 200. If only an antenna (e.g., external antenna assembly 212) is added, the DOI remains the same, however, the effective antenna distance to the DOI has been reduced. This reduction of antenna distance to the DOI increases field strength and leads to an improved signal to noise ratio. The external housing 210 allows the dipole of the antenna assembly to become larger and the RF field at the sensitive volume to be stronger. The external housing 210 further acts as a fluid excluder by reducing the amount of conductive borehole fluids present between NMR tool 200 and its sensitive volume, thereby decreasing noise. All of this leads to an improved signal to noise ratio.

Figure 3:
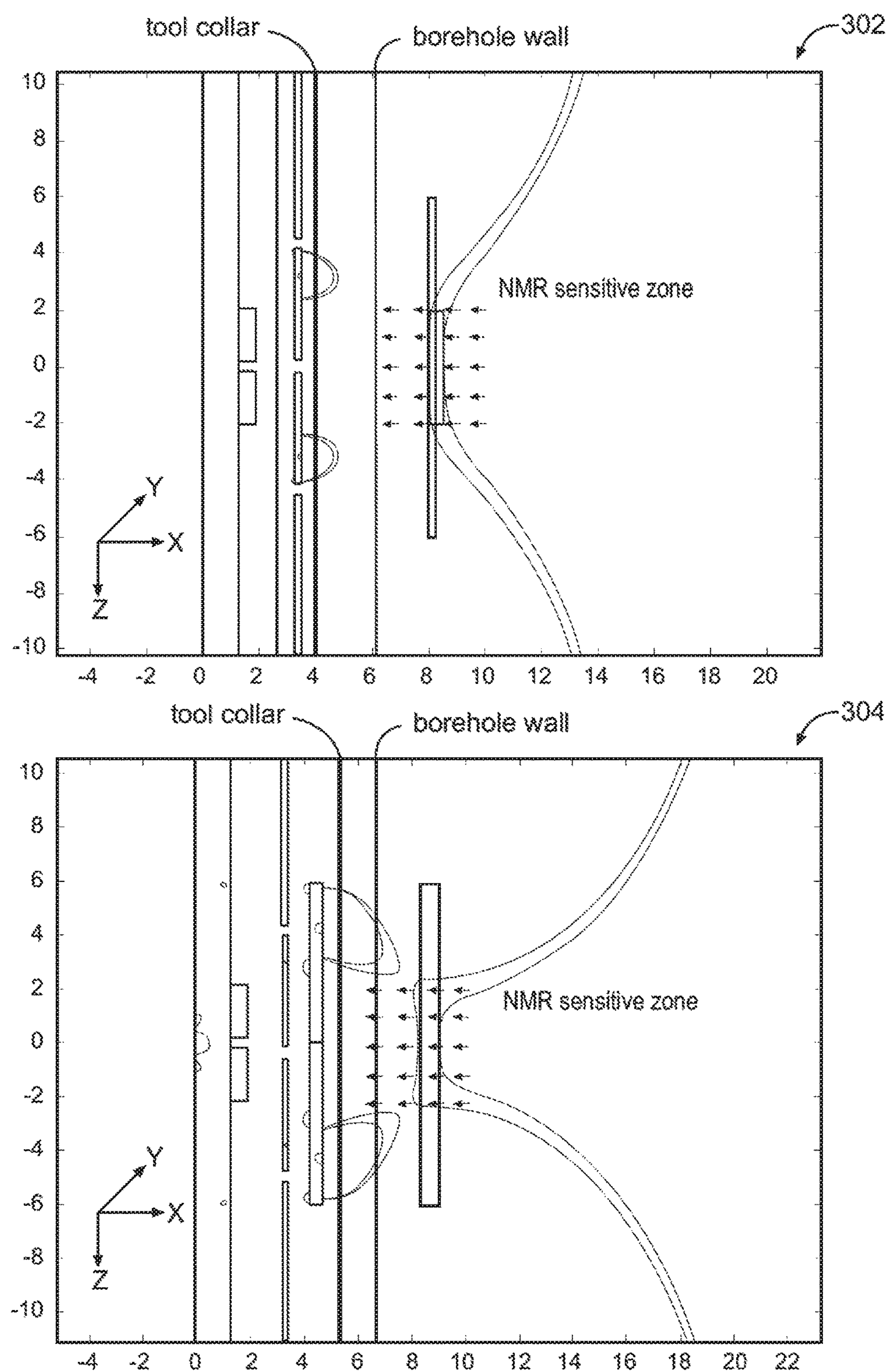
FIG. 3 illustrates side, cut-away views of a portion of a first modeled, radially-symmetric magnetic field profile, according to various embodiments.

FIG. 3 illustrates side, cut-away views 302, 304 of a portion of a modeled, radially-symmetric magnetic field profile, according to various embodiments. In this case, the view 302 corresponds to a modeled magnetic field profile for a NMR logging tool without an external housing. The view 304 corresponds to a modeled magnetic field profile for a NMR logging tool with an external housing, such as the previously-described NMR tool 200 of FIG. 2. For example, in the views 302, 304 the fields are both radially symmetric. Each view shows a slice radially outward and along the logging tool's longitudinal axis 306. For example, in a Cartesian coordinate system, the longitudinal axis 306 can be considered the "Z" direction, and magnetic fields (e.g., produced by antennas of the NMR logging tool) are oriented along the "X" and "Y" directions, respectively. In both views 302 and 304, the magnetic field profiles have a depth of investigation at approximately 8 inches, as measured from the center of the logging tool. It is noted that the views 302, 304 correspond to magnetic fields using the same magnetic configurations. The magnetic fields of views 302 and 304 are similar to each other.

However, the view 304 was modeled for a configuration having a tool outer diameter of approximately 10.625 inches and having a permeable core material added to the logging tool. In other words, the external housing of the logging tool for view 304 includes magnetically permeable material. The addition of the permeable core material changes the magnetic field profile shape of view 304 by a small amount relative to that of view 302. When used in while-drilling applications, such as MWD or LWD, a figure of merit represented by equation (1) can be calculated to estimate the effectiveness or performance of logging tools due to the power-limited nature of drilling tools.

$$SNR/\sqrt{Power} \tag{1}$$

When run in a 12.25 inch borehole, a logging tool having an 8 inch DOI and an 8 inch OD tool collar (e.g., as modeled in view 302) has an estimated figure of merit of approximately 0.034 in a 0.01 Ohm mud. When run in the same 12.25 inch borehole, a logging tool having an 8 inch DOI and a 10.625 inch OD tool collar (e.g., as modeled in view 304) has an estimated figure of merit of approximately 0.43, representing an increase in the figure of merit by at least a factor of ten due to the benefit of having the antenna pushed out closer to the borehole wall and also due to fluid exclusion by having a greater tool outer diameter.

Figure 4:
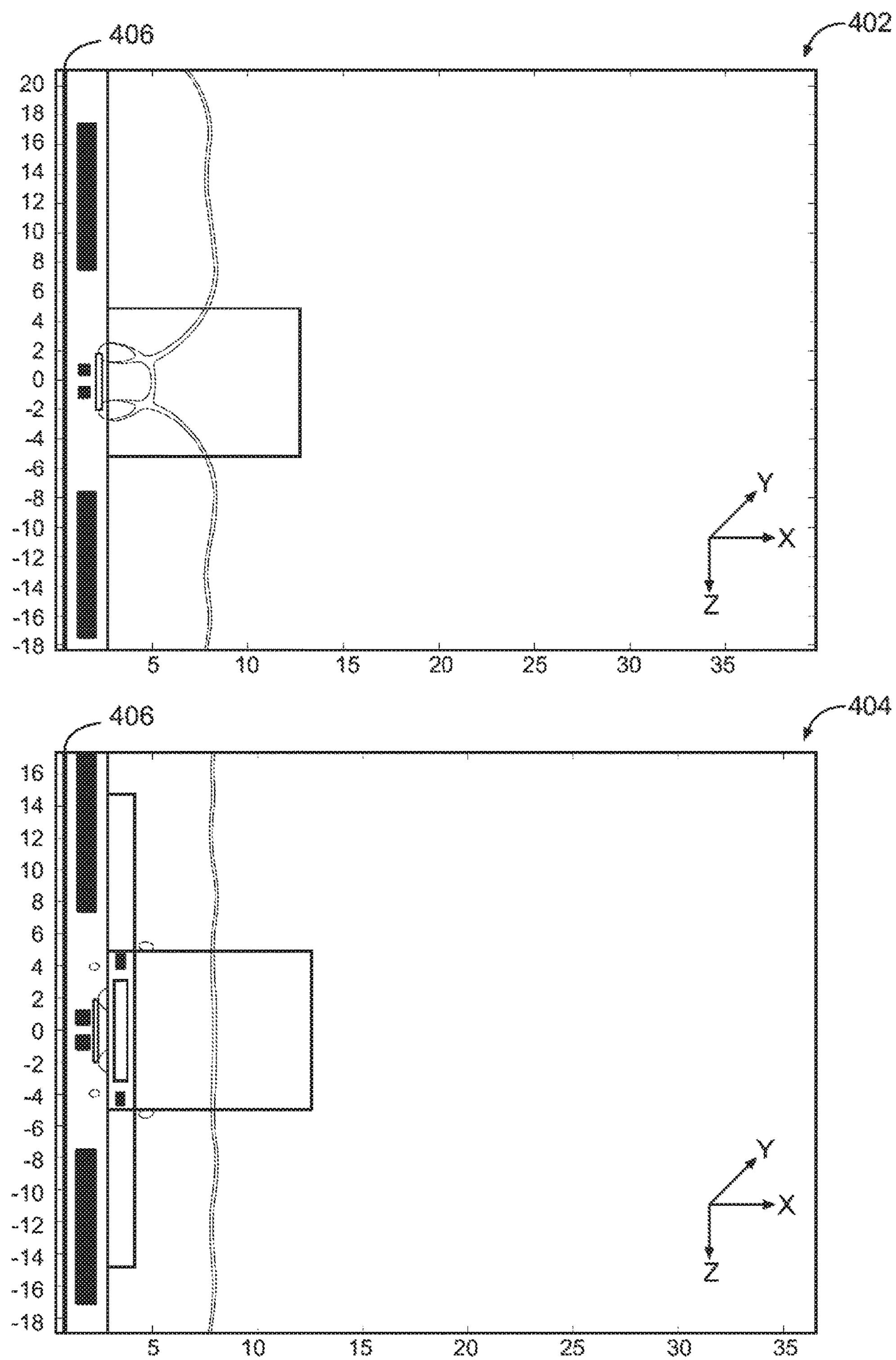
FIG. 4 illustrates side, cut-away views of a portion of a second modeled, radially-symmetric magnetic field profile, according to various embodiments.

FIG. 4 illustrates side, cut-away views 402, 404 of a portion of a modeled, radially-symmetric magnetic field profile, according to various embodiments. In the views 402 and 404, the fields are both radially symmetric. Each view shows a slice radially outward and along the logging tool's longitudinal axis 406. For example, in a Cartesian coordinate system, the longitudinal axis 406 can be considered the "Z" direction, and magnetic fields (e.g., produced by antennas of the NMR logging tool) are oriented along the "X" and "Y" directions, respectively. In this case, the view 402 corresponds to a modeled magnetic field profile for a NMR logging tool without an external housing. In this example, magnets within the NMR logging tool have been configured to generate a field shape that is known to those of ordinary skill in the art as a butterfly type (e.g., view 402) with two saddle points.

The view 404 corresponds to a modeled magnetic field profile for a NMR logging tool with an external housing. In this example, the external housing includes magnets, a permeable material, and an antenna. The magnets in the external housing acts as a shim that adjusts the magnetic field created by the magnet assembly from the configuration without the external housing. In contrast to the example of FIG. 3, the addition of this external housing configuration results in a substantial change in the magnetic field profile shape. The magnetic field of view 404 has been changed by the addition of the external housing to create a long symmetrical field at an approximate depth of investigation of 8 inches (e.g., 4 inches into the formation). This extended field is less susceptible motion effects, but has a smaller cross section. This can lead to a decrease in signal strength, and thus a smaller signal to noise ratio can be experienced as well.

In other embodiments, the configuration of components in the external housing can be adjusted to maintain the magnetic field profile, but with a shallower depth of investigation. In another embodiment, if the NMR logging tool's sensitive volume is already working at a certain depth of investigation, changing the sensitive volume allows for running the tool in a larger borehole without changing the tool's electronics. By keeping the frequency the same at the volume of interest (e.g., at a DOI of 2 inches for a slim borehole and 4 inches for a larger borehole), the same electronics can be used for both configurations.

It is noted that this disclosure is not limited to the specific examples illustrated and discussed in relation to FIGS. 3 and 4. Rather, other embodiments can utilize the disclosed external housing for NMR logging operations. In one embodiment, the external housing can further include a spoiling antenna (e.g., in addition to any existing RF/NMR antenna) to remove unwanted signals. For example, unwanted signals can include borehole signals or signals from Na (e.g., Sodium-23 ions). The spoiling antenna provide an additional DC or AC field which reduces unwanted signals. These spoiling antennas are often put in an opposing position to other antennas. For example, if a wireline tool has a front facing antenna, one that is nearest to the formation, a spoiling antenna would be placed on the back of the tool. For a drilling tool, the antenna might be placed in a differing direction or much further up along the tool. That is, if a drilling tool had a solenoid (otherwise known as a monopole type), a transversal or longitudinal antenna can be placed under it. Alternatively, a second solenoid can be placed above or below the solenoid. In another embodiment, the external housing can further include at least one of an electrical coil or another magnetic assembly for generating a gradient field, allowing the NMR logging tool to be switchable between a low gradient tool to a high gradient tool.

In another embodiment, all components (e.g., sonde magnet, antenna, and permeable material) of the NMR logging tool are positioned within the external housing. In this way, the tool dimensions remain stationary and specific excluders are positioned on the outside for particular borehole sizes. Alternatively, the external housing may only include magnets, with any other sensor components (e.g., antenna or permeable material) contained within the NMR tool housing (e.g., a sonde).

In another embodiment, both the NMR logging tool and external housing contain NMR tool components. The magnetic field generated by such a tool can be significantly changed or only slightly adjusted, depending on the specific configuration of the tool's components. For example, the tool can contain more than one antenna. These antennas can produce orthogonal or parallel fields, transmitted in or out of phase, operate in a common sensitive volumes or in separate sensitive volumes.

In summary, positioning at least a portion of the NMR logging tool components (e.g., magnet, antenna, or permeable material) in an external housing allows for increased signal strength and decreased noise, resulting in increased SNR. The external housing further enables the ability to work in multiple borehole sizes by adjusting magnetic fields.

Figure 5:
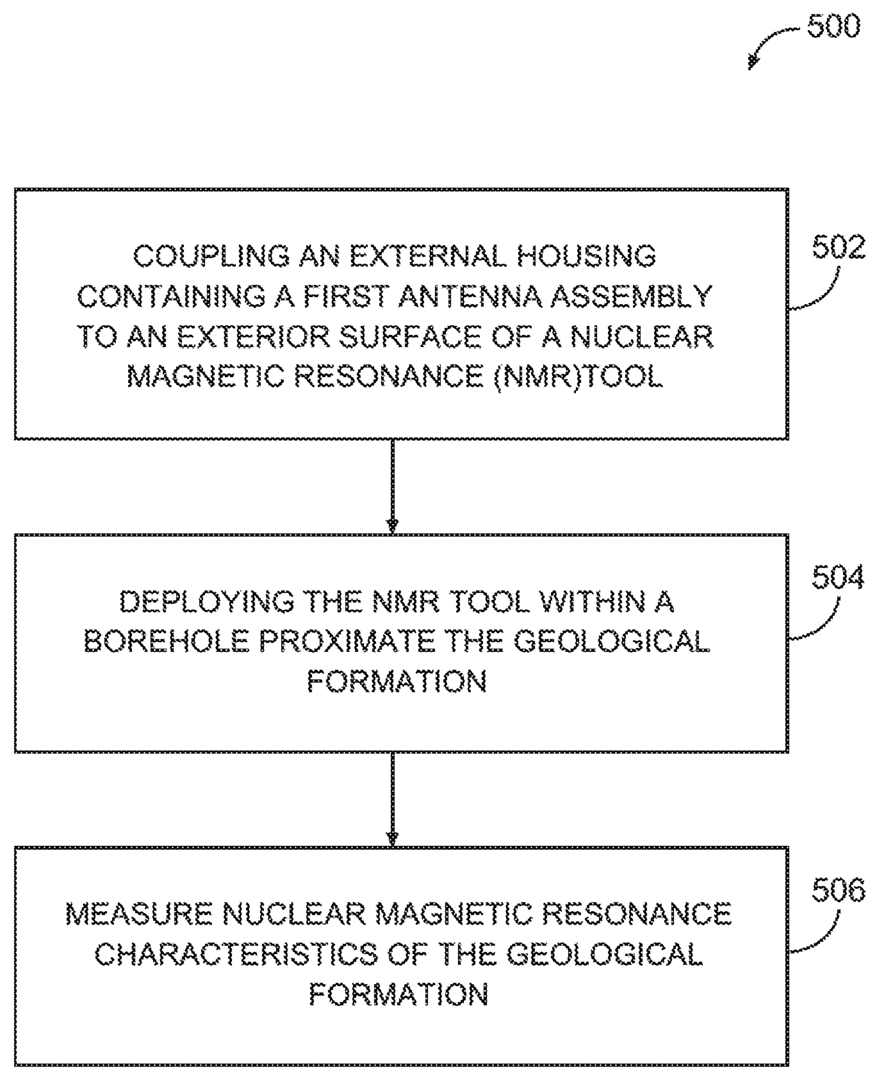
FIG. 5 is a flow chart illustrating a method for operating a NMR tool, according to one or more embodiments.

FIG. 5 illustrates a method 500 for operating a NMR tool, according to one or more embodiments. Method 500 begins at operation 502 by removably coupling an external housing containing a first antenna assembly to an exterior surface of a NMR tool. The NMR tool includes a second antenna assembly and a magnet assembly, and is configured to perform logging operations by generating a sensitive volume in a geological formation when the NMR tool is positioned downhole in a borehole. In some embodiments, the external housing further contains at least one of an external magnet assembly or a magnetically permeable material. The presence of such components operate to modify the magnetic field generated by the magnetic assembly of the NMR tool and thus changes the sensitive volume of the NMR tool.

The method 500 continues at operation 504 by deploying the NMR tool within a borehole proximate to the geological formation to be measured. It is noted that coupling the external housing to the NMR tool results in positioning a receiver and/or transmitter (e.g., the first antenna assembly) closer to the sensitive volume. Further, coupling the external housing to the NMR tool increases the outer diameter of the apparatus and excludes a volume of fluid in the borehole between the NMR tool and borehole wall. The method 500 concludes at operation 506 by measuring nuclear magnetic resonance characteristics of the geological formation. It is noted that due to the antenna assembly being positioned closer to the formation and further due to a smaller volume of fluid in the borehole where measurements are being taken, a higher signal to noise ratio is achieved.

To better illustrate the apparatus and systems disclosed herein, a non-limiting list of examples is provided:

Example 1 can include an apparatus, comprising: a nuclear magnetic resonance (NMR) tool that includes a first antenna assembly and a magnet assembly disposed within a tool housing to produce a magnetic field in a volume in a geological formation; and an external housing removably coupled to an exterior surface of the tool housing, wherein the external housing comprises a second antenna assembly.

Example 2 can include, or can optionally be combined with the subject matter of Example 1, wherein the external housing further comprises a magnetically permeable material.

Example 3 can include, or can optionally be combined with the subject matter of Example 1, wherein the second antenna assembly comprises a transversal-dipole antenna or a longitudinal-dipole antenna.

Example 4 can include, or can optionally be combined with the subject matter of Example 1, wherein the second antenna assembly is communicably coupled to a lead from within the tool housing.

Example 5 can include, or can optionally be combined with the subject matter of Example 1, wherein the magnet assembly comprises multiple unitary ring-shaped elements and/or a series of rectangular elements placed into a ring-shaped arrangement.

Example 6 can include, or can optionally be combined with the subject matter of Example 1, wherein the first antenna assembly is deactivated when the second antenna assembly is communicably connected to the tool housing.

Example 7 can include, or can optionally be combined with the subject matter of Example 1, wherein the external housing further comprises a second magnet assembly.

Example 8 can include, or can optionally be combined with the subject matter of Example 1, wherein the external housing further comprises a spoiling antenna.

Example 9 can include, or can optionally be combined with the subject matter of Example 1, wherein the external housing further comprises at least one of an electrical coil or a second magnetic assembly for generating a gradient field.

Example 10 can include a system, comprising: a magnet assembly to produce a magnetic field in a volume in a geological formation; a downhole tool attached to the magnet assembly, the downhole tool comprising a transmitter and a receiver to excite and receive a nuclear magnetic resonance response in the magnetic field; and an external housing removably coupled to an exterior surface of the downhole tool, wherein the external housing comprises a first antenna assembly.

Example 11 can include, or can optionally be combined with the subject matter of Example 10, wherein the downhole tool comprises one of a wireline tool or a drilling tool.

Example 12 can include, or can optionally be combined with the subject matter of Example 10, wherein the external housing further comprises a magnetically permeable material.

Example 13 can include, or can optionally be combined with the subject matter of Example 10, wherein the first antenna assembly comprises a transversal-dipole antenna or a longitudinal-dipole antenna.

Example 14 can include, or can optionally be combined with the subject matter of Example 10, wherein the first antenna assembly is communicably coupled to a lead from within the tool housing.

Example 15 can include, or can optionally be combined with the subject matter of Example 10, wherein the magnet assembly comprises multiple unitary ring-shaped elements and/or a series of rectangular elements shaped to form a ring.

Example 16 can include, or can optionally be combined with the subject matter of Example 10, wherein the tool housing includes an inner antenna assembly that is deactivated when the first antenna assembly is communicably connected to the tool housing.

Example 17 can include, or can optionally be combined with the subject matter of Example 10, wherein the external housing further comprises a second magnet assembly.

Example 18 can include, or can optionally be combined with the subject matter of Example 10, wherein the external housing further comprises a spoiling antenna.

Example 19 can include, or can optionally be combined with the subject matter of Example 10, wherein the external housing further comprises at least one of an electrical coil or a second magnetic assembly for generating a gradient field.

Example 20 can include a method, comprising: removably coupling an external housing containing a first antenna assembly to an exterior surface of a nuclear magnetic resonance (NMR) tool, wherein the NMR tool includes a second antenna assembly and a magnet assembly to generate a sensitive volume in a geological formation; deploying the NMR tool within a borehole proximate the geological formation; and measuring nuclear magnetic resonance characteristics of the geological formation.

Example 21 can include, or can optionally be combined with the subject matter of Example 20, further comprising: changing the sensitive volume of the NMR tool using at least one of an external magnet assembly or a magnetically permeable material positioned within the external housing.

Example 22 can include, or can optionally be combined with the subject matter of Example 20, wherein removably coupling the external housing to the NMR tool reduces signal noise by excluding a volume of fluid in the borehole between the NMR tool and the geological formation.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The embodiments are submitted with the understanding that they will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. An apparatus, comprising:

a nuclear magnetic resonance (NMR) tool that includes a deactivated first antenna assembly and a magnet assembly disposed within a tool housing to produce a magnetic field in a volume of a geological formation; and an external housing removably coupled to an exterior surface of the tool housing, wherein the external housing comprises a second antenna assembly, the second antenna assembly disposed radially outward of the first antenna assembly.

2. The apparatus of claim 1, wherein the external housing further comprises a magnetically permeable material.

3. The apparatus of claim 1, wherein the second antenna assembly comprises a transversal-dipole antenna or a longitudinal-dipole antenna.

4. The apparatus of claim 1, wherein the second antenna assembly is communicably coupled to a lead from within the tool housing.

5. The apparatus of claim 1, wherein the magnet assembly comprises multiple unitary ring-shaped elements and/or a series of rectangular elements placed into a ring-shaped arrangement.

6. The apparatus of claim 1, wherein the external housing further comprises a spoiling antenna.

7. The apparatus of claim 1, wherein the external housing further comprises at least one of an electrical coil or a second magnetic assembly for generating a gradient field.

8. The apparatus of claim 1, wherein the external housing extends to a greater outer diameter than an outer diameter of the tool housing.

9. A system, comprising:

a magnet assembly to produce a magnetic field in a volume in a geological formation;

a downhole tool attached to the magnet assembly, the downhole tool comprising a tool housing and first antenna assembly disposed within the tool housing, the first antenna operable with a transmitter and a receiver respectively to excite and receive a nuclear magnetic resonance response in the magnetic field, wherein at least one of the transmitter and receiver is deactivated; and an external housing removably coupled to an exterior surface of the tool housing of the downhole tool, wherein the external housing comprises a second antenna assembly, the second antenna assembly disposed radially outward of the first antenna assembly.

10. The system of claim 9, wherein the downhole tool comprises one of a wireline tool or a drilling tool.

11. The system of claim 9, wherein the external housing further comprises a magnetically permeable material.

12. The system of claim 9, wherein the second antenna assembly comprises a transversal-dipole antenna or a longitudinal-dipole antenna.

13. The system of claim 9, wherein the second antenna assembly is communicably coupled to a lead from within the tool housing.

14. The system of claim 9, wherein the magnet assembly comprises multiple unitary ring-shaped elements and/or a series of rectangular elements shaped to form a ring.

15. The system of claim 9, wherein the external housing further comprises a spoiling antenna.

16. The system of claim 9, wherein the external housing further comprises at least one of an electrical coil or a second magnetic assembly for generating a gradient field.

17. A method, comprising:

removably coupling an external housing containing a deactivated first antenna assembly to an exterior surface of a nuclear magnetic resonance (NMR) tool, wherein the NMR tool includes a second antenna assembly and a magnet assembly to generate a sensitive volume in a geological formation, and wherein the second antenna assembly is disposed radially outward of the first antenna assembly when the external housing is coupled to the NMR tool;

deploying the external housing coupled to the NMR tool within a borehole with the external housing proximate the geological formation; and measuring nuclear magnetic resonance characteristics of the geological formation with the second antenna assembly.

18. The method of claim 17, further comprising: changing the sensitive volume of the NMR tool using at least one of an external magnet assembly or a magnetically permeable material positioned within the external housing.

19. The method of claim 17, wherein removably coupling the external housing to the NMR tool reduces signal noise by excluding a volume of fluid in the borehole between the NMR tool and the geological formation.

20. The system of claim 9, wherein the external housing extends to a greater outer diameter than an outer diameter of the tool housing.

* * * * *

UNITED STATES PATENT AND TRADEMARK OFFICE

CERTIFICATE OF CORRECTION

PATENT NO. : 10,422,915 B2
APPLICATION NO. : 15/524955
DATED : September 24, 2019
INVENTOR(S) : Rebecca Corina Jachmann, Jie Yang and Daniel Lee Miller It is certified that error appears in the above-identified patent and that said Letters Patent is hereby corrected as shown below:

In the Specification

In Column 1 after the title, please add:
--PRIORITY
The present application is a U.S. National Stage patent application of International Patent Application No. PCT/US2015/067852, filed on December 29, 2015, the benefit of which is claimed and the disclosure of which is incorporated herein by reference in its entirety.--

Signed and Sealed this
Eleventh Day of February, 2020

Andrei Iancu
*Director of the United States Patent and Trademark Office*